United States Patent [19]
Cape

[11] Patent Number: 5,373,847
[45] Date of Patent: Dec. 20, 1994

[54] METHOD OF COLOR DOPPLER MAPPING OF BLOOD FLOW IN A PATIENT

[75] Inventor: Edward G. Cape, Pittsburgh, Pa.

[73] Assignee: University of Pittsburgh of the Commonwealth System of Higher Education, Pittsburgh, Pa.

[21] Appl. No.: 974,408

[22] Filed: Nov. 12, 1992

[51] Int. Cl.$^5$ .............................................. A61B 8/06
[52] U.S. Cl. .............................................. 128/661.09
[58] Field of Search .......... 128/660.05, 661.08–661.10; 73/861.25

[56] References Cited

U.S. PATENT DOCUMENTS

| | | | |
|---|---|---|---|
| 4,761,740 | 8/1988 | Lipschutz | 128/660.05 X |
| 4,932,415 | 6/1990 | Augelsen et al. | 128/661.07 |
| 5,042,491 | 8/1991 | Amemiya | 128/661.09 |
| 5,105,817 | 4/1942 | Uchibori et al. | 128/661.08 |
| 5,190,044 | 3/1993 | Kawasaki et al. | 128/660.05 X |

OTHER PUBLICATIONS

Greene, F. M. et al "Computer-Based Pattern Recognition of Carotid Arterial Disease Using Pulsed Doppler UTS", UTS in Med & Biol. vol. 8 No. 2 pp. 161–176 1982.

Primary Examiner—Francis Jaworski
Attorney, Agent, or Firm—Arnold B. Silverman; David V. Radack

[57] ABSTRACT

The method for imaging vascular blood flow in a patient includes the steps of emitting ultrasound energy from a transducer with at least a portion of said ultrasound energy being reflected back towards the transducer, monitoring the reflected energy over time, calculating blood flow velocity in at least a portion of a patient's vascular system, filtering all velocities equal to or below the calculated or predetermined velocity to allow a high velocity locus to be defined, and producing a color Doppler flow map of the filtered velocity.

10 Claims, 2 Drawing Sheets

METHOD OF COLOR DOPPLER MAPPING OF BLOOD FLOW IN A PATIENT

BACKGROUND OF THE INVENTION

1. Field of the Invention

The present invention relates to an improved method for color Doppler flow mapping of cardiac blood flow.

2. Description of the Related Art

Color Doppler flow mapping was developed in the early 1980's as a two dimensional extension of the basic pulsed wave Doppler ultrasound concept. In clinical application, Doppler ultrasound instruments allow noninvasive measurement of blood cell velocities, in which ultrasound waves (>20,000 Hz) are emitted from a transducer and pass into the cardiac chambers where they strike moving blood cells. Part of the ultrasonic wave is then reflected back to the transducer. The frequency of emitted sound is known and the frequency of the returning signal is measured. The Doppler principle then allows conversion of this frequency shift into the blood cell velocity by the equation $$V = (cf_d)/(2f_o COS\theta) \quad (1)$$

where
- v = Velocity of the target
- c = Speed of sound in the medium (approx. 1540 m/s in tissue/blood)
- $f_d$ = Frequency shift, or Doppler shift, equal to frequency difference between emitted and reflected sound
- $f_o$ = Emitted frequency
- $\theta$ = The Angle between ultrasound beam path and blood cell velocity vector By pulsing a burst of ultrasound, waiting a time t and then monitoring the returning signal, the depth from which the signal must have returned can be calculated as $$D = c(\Delta t)/2 \quad (2)$$

where
- c = speed of sound in the medium
- $\Delta t$ = time between emission and reception of sound Conventional pulsed wave Doppler ultrasound refers to application of this principle to measurement of velocity in a single sample volume at a desired distance away from the transducer. Color Doppler flow mapping allows extension of the concept to provide a matrix of velocities as follows. A burst of ultrasound is emitted and then monitored incrementally as it returns, basically dividing the $\Delta t$ in equation (2) into intervals and providing velocities at a series of locations along a single line. This "string" of sample velocities is then sequentially refocused through a range of angles from a multi-crystal transducer, ultimately resulting in a pie shaped matrix of velocities. This pie shaped matrix can be updated 8 to 30 times in a second with conventional instruments. As it is not possible to examine individual spectra from the thousands of measurement locations, velocities are averaged within a sample volume and color coded using a predetermined color bar. These color coded velocities are then finally superimposed on an echocardiographic image, which may be thought of as an ultrasound "radar" providing position data on solid cardiac structures.

A significant contribution of this technology is in the detection of abnormal lesions in heart disease. For example, the basic function of a heart valve is to allow forward flow with little obstruction when the valve is open and to prevent backflow when closed. Valves often develop lesions or close improperly, allowing undesired blood to pass in a reverse direction across the valve. Fluid mechanically this condition is reflected by a turbulent jet which in the setting of mitral regurgitation, for example, would emerge from a leaking mitral valve and enter the left atrium. On a color Doppler flow map the condition is reflected by a multicolored jet-type image in the left atrium. Two factors influence the image produced. First, the entire receiving chamber is filled with nonzero velocities and in light of the above explanation, the entire chamber should be filled with color, but it is not. Instead, a tear-drop shaped jet appears. Second, this shape appears because of a high pass filter present in the data processing circuitry of the instrument.

This high pass filter, referred to as a wall filter, is set so as to eliminate low frequency, high amplitude signals returning from cardiac structures. In other words, the moving structures have nonzero velocity just as the blood cells do and therefore produce an appreciable Doppler shift. However, due to the large size of the structures (on the order of centimeters) compared to blood cells (on the order of microns), they send signals back to the transducer which have a very high amplitude and these signals can saturate image processing circuitry. These filters were employed in conventional pulsed wave Doppler equipment in order to eliminate the noise produced by the moving cardiac structures. With the advent of color flow mapping the filters naturally carried over as the threshold which defines a color jet boundary. Detected frequency shifts above the filter receive color encoding, and those below it do not.

The ability to visualize regurgitant jets with color Doppler flow mapping led to great enthusiasm in the mid-eighties. In numerous studies, jet size by color Doppler was related to the severity of regurgitation and compared to the gold standard of catheterization. Planimetered jet areas became commonly used in many centers at least as a marker of the severity of regurgitation. However, studies over the last four to five years have revealed that such an approach is dangerous due to the fact that jet size determined by color Doppler is tremendously variable as a function of factors which are independent of regurgitant flow. These factors are both (a) technical, such as gain settings, frame sampling rate, and (b) physical in nature, such as driving pressure, interrupting flows, heart rate interaction with frame rate. Approaches based on engineering principles of conservation of momentum and mass have been advanced, but have been difficult to apply in the clinical setting Furthermore, the clinician is more inclined to embrace a technique requiring simplified measurements of jet area as opposed to one which requires more cumbersome engineering calculations.

Current filter settings are chosen to eliminate noise resulting from cardiac structures. This unfortunately results in the jet boundaries being defined in relatively unstable portions of the jet.

There remains, therefore, a substantial need for a method of color Doppler mapping of cardiac blood flow and other vascular blood flow, which eliminates the problems set forth hereinbefore.

SUMMARY OF THE INVENTION

As used herein "patient" shall mean members of the animal kingdom, including humans and fetuses.

As used herein, the term "vascular blood flow" shall mean blood flow within a vascular component of a patient including but not limited to cardiac blood flow.

The present invention has met the above need. The method for imaging blood flow includes the steps of emitting ultrasound energy from a transducer with at least a portion of said ultrasound energy being reflected back towards the transducer, monitoring the reflected energy over time, calculating jet velocity in at least a portion of a patient's heart, filtering all velocities equal to or below the calculated velocity to allow a high velocity locus to be defined, and producing a color DoppLer flow map of the filtered velocity.

It is an object of the present invention to provide an improved method of color Doppler mapping of vascular blood flow in a human being.

It is a further object of this invention to provide such a method that may be improved to resist technical and physical factors that tend to interfere with the consistency of color Doppler mapping.

It is yet another object of the present invention to provide such a method which eliminates much of the variability associated with jet planimetry techniques.

It is another object of the present invention to provide such a method which will be capable of improved monitoring of cardiac valve blood regurgitation.

These and other objects of the invention will be more fully understood from the following description of the invention on reference to the illustrations appended hereto.

DESCRIPTION OF THE PREFERRED EMBODIMENTS

As employed herein, the expression "jet" shall mean the flowing blood stream or portion thereof being discussed as distinguished from the blood vessel within which flow occurs.

The filter settings of the present invention are based on fluid mechanical principals and results in filters well above those used in present instruments. This is because the choice of filters with the method of the present invention will be made based on fundamentally different considerations from those used to establish present filters. When referring to the jet boundary herein, to avoid confusion, the term "wall filter" is employed throughout this disclosure.

Filters in accordance with the present invention are selected to define the jet boundary along a locus which encloses a region of high jet momentum. Specific choice of the velocity will depend on the situation at hand just as current instruments require a choice based on solid wall motion. It is presently preferred to select a jet having a velocity of at least about 30 centimeters per second and most preferably about 30 to 50 cm/sec.

Figure 1:
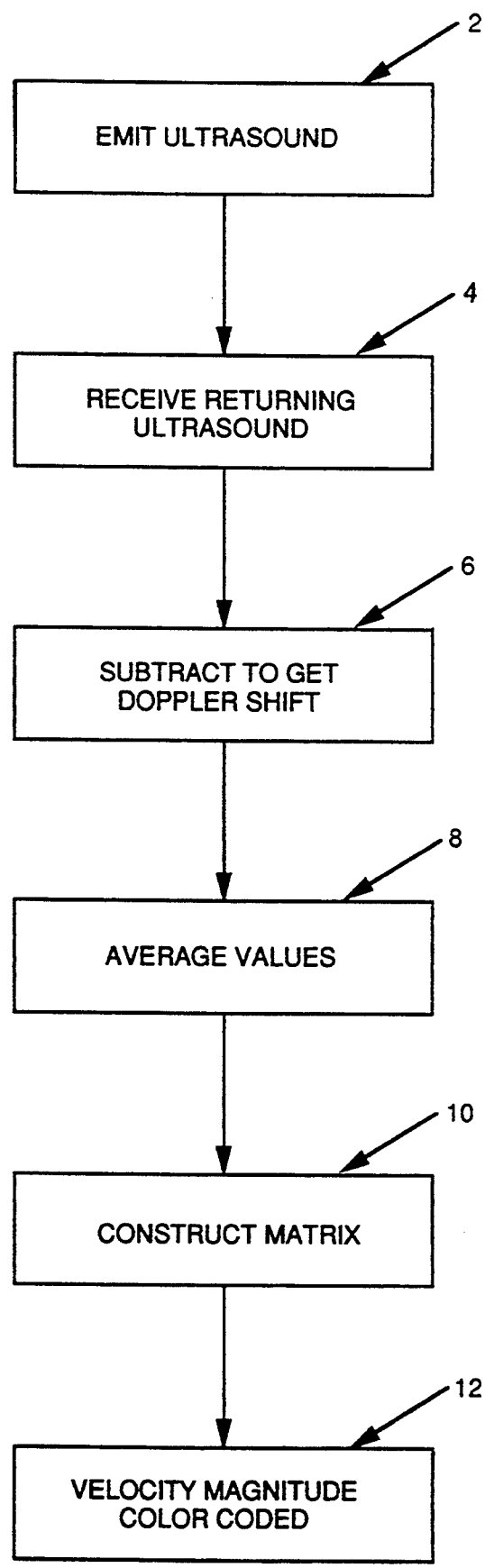
FIG. 1 is a schematic flow diagram illustrating a sequence of events employed in a method of the invention.

Referring to FIG. 1, there is shown schematically a Doppler system employable with the present invention. In a preferred practice of the invention, in monitoring cardiac blood flow, a transducer is appropriately directed toward the blood vessel adjacent the cardiac valve wherein flow is to be monitored. Pulsed ultrasound energy is emitted 2. It impinges upon the jet with portions of the ultrasonic energy being returned 4 to the transducer. Subtraction 6 of the frequency of returned sound from the known frequency of emitted sound yields, the Doppler shift $f_d$ which is to be used in equation (1). A plurality of sample values of the Doppler shift are averaged 8 to get a single sample velocity in order to determine a single velocity value for the moving bloodstream. By multigating and focusing the ultrasonic energy through a range of angles in a conventional manner, construction of a matrix 10 of sample velocities may be achieved. Based upon velocity magnitudes, color coding is effected 12. Velocities below the predetermined desired wall filter level, although greater than 0, do not receive a color. Those which are given a color permit use of the high velocity portion of the jet in accurately determining cardiac vascular blood flow within the context of the present invention.

Figure 2:
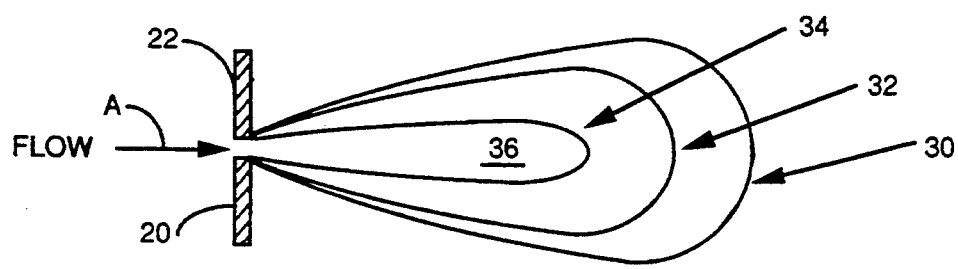
FIG. 2 is a schematic illustration of velocity profiles of blood flow.

Referring now to FIG. 2, blood flow through an aperture 20 in a plate 22 is schematically illustrated occur in the direction of the arrow A. Line 30 represents a conventional low velocity flow which may be on the order of about 5 to 15 cm/sec. Line 32 represents medium velocity on the order of greater than about 15 to 24 cm/sec. Line 34 represents high velocity flow on the order of at least about 30 cm/sec and preferably in the range of about 30 to 50 cm/sec as contemplated by the present invention. More specifically, the zone between lines 30 and 32 will be as low velocity, the zones between line 32 and 34 will be at medium velocity and the region 36 defined between line 34 and plate 22 will be at the high velocity. It is the jet flow within area 36 which may be measured by the present invention as a result of the wall filter selecting high velocity and thereby minimizing inaccuracies due to both physical and technical factors which have interfered with prior art efforts to achieve an accurate and reliable cardiac flow monitoring. It will be appreciated, therefore, that the present method, from its determination of the desired high velocity wall filter which eliminates many negative factors of the prior art that interfere with obtaining an accurate reading of blood flow velocity.

Figure 3:
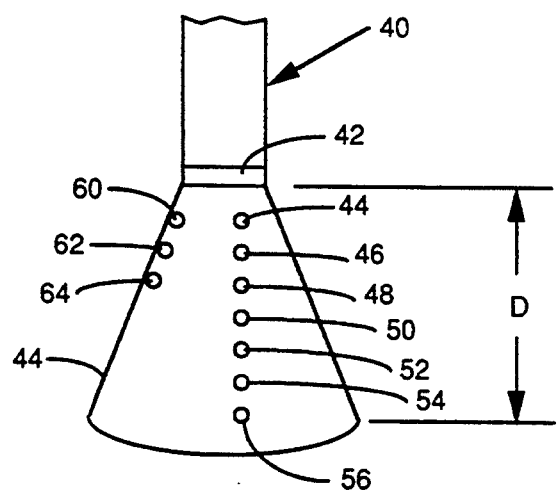
FIG. 3 is a schematic illustration of the ultrasonic transducer employed in the invention.

Referring to FIG. 3, there is shown ultrasonic apparatus 40 which contains a transducer 42 which is adapted to emit a generally triangular ultrasonic pulsed wave 44 having a dimension D which may for typical cardiac monitoring uses range from about 5 cm for pediatric use to about 15 cm for adult use. Shown schematically within the ultrasonic energy 44 are a plurality of blood cells or cell clusters 44, 46, 48, 50, 52, 54, 56 disposed in generally linear relationship. It will be appreciated that a large number of such rows, such as that shown in part by reference numbers 60, 62, 64, will be contained within the energized zone 44. For simplicity of illustration, only a sampling has been illustrated. The elapsed time between the pulsing of the ultrasonic energy and the return of a given wave energy permits determination of the position of the object and the Doppler shift monitoring permits velocity determination. In this manner, the matrix discussed hereinbefore may be established.

Figure 4:
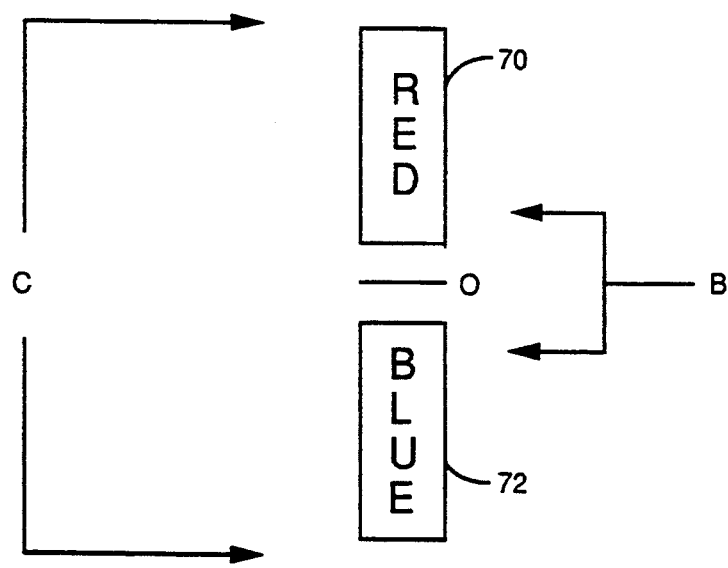
FIG. 4 illustrates schematically a color velocity reference bar employed in color Doppler mapping.

Referring to FIG. 4 there is shown schematically the color zones which represent conversion of velocity values in the color Doppler monitoring method. The 0 level is indicated and the region of influence of the wall filter is represented by the bracketed region B. Velocities within this zone B will be filtered out and not converted to a color representation. For example, in the preferred embodiment of the invention velocities which are not above 30 cm/sec will not be represented by either the color red or blue. In addition, the outer limits as shown by bracketed portion C shown the Nyquist limit which establishes the outer confines of the readings in order to eliminate undesired distortions in the data due to use of a sampling frequency which is typically about 4KH$_z$. Velocities which flow in the red zone 70 indicate flow in a first direction, and velocities which flow in the blue zone indicate flow in a positive direction toward the transducer, and velocities which flow in the blue zone 72 indicated flow in the opposite direction. The intensity of the color is directly related to the velocity of flow.

An example will be given to demonstrate the selection of filters in the present invention. In the case of mitral regurgitation with strong counterflow produced by pulmonary venous inflow, inflow momentum can be calculated from inlet velocities squared multiplied by approximate inlet areas available either from two-dimensional echocardiography or the width of color on the inflow map. The filter setting is then adjusted to a frequency/velocity above the value. This will result in filtering out velocities below the selected value. This facilitates obtaining the desired image of the jet. In this way, weak, low momentum velocities along the fringes of the jet will be trimmed for constant regurgitant flow at the orifice as demonstrated in previous studies. Reducing the jet (in the absence of counterflow) to the area defined by a higher momentum locus will allow the jet to be maintained in the face of the counterflow.

Defining the jet boundary by a high momentum locus in this manner reduces variability due to technical factors, such as, for example, frame rate As those skilled in the art know, decreased frame rate or increased heart rate reduces the apparent maximum color Doppler jet area for constant peak regurgitant flows by reducing the probability that the maximum physical flow will be detected by the sweeping Doppler scan line. Shifting the jet boundary inward by elevating the wall filter to a high momentum locus isolates a physical portion of the jet which penetrates the receiving chamber quickly. Having established the size of this baseline jet at a higher frame rate or lower heart rate, sequential increases in heart rate or decreases in frame rate while peak flow is maintained constant will then produce less of an undesired effect on the higher filter level jet. An advantage of the present invention is the substantial reduction or elimination of the adverse effects of changes in gain interrupting flow (including co-flow) frame rate and heart rate.

EXAMPLE

In order to confirm that the invention's use of a high pass velocity filter ("wall filter") will produce a more robust color Doppler jet area in the face of previously demonstrated causes of variability tests were performed. A first series of tests were performed employing constant flow turbulent jets which were water containing suspended ultrasonically opaque starch particles flowing in an acrylic tube having a chamber of an internal diameter of about 6 cm with a 3 mm internal diameter orifice employing velocities of 1.5, 3.0 and 4.5 meters/second at four gain levels, i.e., instrument settings of 1, 5, 10, 16. A second series of tests were performed employing pulsatile jets having a 3 mm internal diameter orifice employing peak velocities of 3 and 6 meters/second at four gain levels, i.e., instrument settings, i.e., 1, 5, 10, 16. In order to reduce or eliminate variations caused by the specific equipment employed, all of the tests were performed a first time using the Toshiba 160 Doppler instrument and a second time employing the Hitachi CVC 151 Doppler instrument. The correlation between the two instruments was excellent and confirmed the general operability of the method of the invention. More specifically, for a given flow condition, changes in color Doppler jet area (CJA) with gain were tested with increasing wall filter settings within the available range settings of each instrument. The total experiments involved 72 combinations of velocities, gains and wall filter settings. CJA correlated well (r greater than 0.9) and increased with increasing gain (G) for all experiments. Slopes of regression lines (CJA v. G) decreased with increasing wall filter for all experiments. On average, the percentage increase in CJA with gain for low wall filter was 2.38 times greater than for the high wall filter. As stated hereinbefore, the high wall filter use of high velocity reduces the inadequacies of the prior art. This, therefore, demonstrates that more consistent images of vascular blood flow, such as regurgitation can be achieved with higher wall filter.

While it will be appreciated that the preferred method of the present invention involves calculating average blood flow velocity for the specific patient being tested and then employing high velocity as a threshold for information gathering, if desired the high velocity threshold which may, for example, be greater than about 30 cm/sec may be employed for a large number of patients without individual predetermination. This approach, however, is not preferred.

Another advantage of the method of the present invention is that it can be employed with existing Doppler instruments which may be modified to achieve the desired high wall filter through a software and/or hardware modification which may be made readily by those skilled in the art.

It will be appreciated that the invention facilitates measurement in the center regions of flow and thereby minimizes undesired variability due to turbulence and other fluid mechanic considerations. A color Doppler flow map of the filtered velocity can be prepared if desired.

Whereas particular embodiments of the invention have been described above for purposes of illustration, it will be evident to those skilled in the art that numerous variations of the details may be made without departing from the invention as defined in the appended claims.

I claim:

1. A method for imaging vascular blood flow velocity in a patient comprising
    emitting ultrasonic energy from a transducer at a particular frequency into a portion of a patient's vascular system with at least a portion of said ultrasonic energy being reflected back towards said transducer, monitoring said reflected energy detected by said transducer over time wherein said monitored energy at each increasing time interval is indicative of reflections at increasingly greater distances from said transducer, detecting shifts in frequency of said reflected energy with respect to said emitted energy frequency, said frequency shifts represented by frequency signals, each of which are proportional to blood flow velocity in said portion of said patient's vascular system, filtering said frequency signals corresponding to said velocities below a pre-selected value, calculating an average blood flow velocity based on said filtered frequencies, and creating a matrix of sample velocities based on a plurality of said average blood flow velocities.

2. The method of claim 1 including the further step of producing a color Doppler flow map based on said matrix.

3. The method of claim 2 including filtering velocities below above 30 cm/sec.

4. The method of claim 1 including by said method selecting a jet for velocity monitoring which is a center portion of said blood stream, whereby accuracy of said imaging will be enhanced.

5. The method of claim 4 including monitoring in said jet velocities greater than about 30 cm/sec.

6. The method of claim 5 including monitoring said jet velocity in the range of about 30 to 50 cm/sec.

7. The method of claim 1 including specifically determining the velocity level below which velocities will be filtered for the specific patient being treated.

8. The method of claim 1 including determining the velocity level below which velocities will be filtered and employing said determination for a plurality of patients.

9. A method for imaging vascular blood flow in a patient comprising method for imaging vascular blood flow in a patient comprising emitting ultrasonic energy from a transducer at a particular frequency into a portion of a patient's vascular system with at least a portion of said ultrasonic energy being reflected back towards said transducer, monitoring said reflected energy detected by said transducer over time wherein said monitored energy at each increasing time interval is indicative of reflections at increasingly greater distances from said transducer, detecting shifts in frequency of said reflected energy with respect to said emitted energy frequency, calculating an average blood flow velocity based on said frequency shifts, creating a matrix of sample velocities based on a plurality of said average blood flow velocities, said matrix of sample velocities containing a high velocity locus of said vascular blood flow, filtering velocities equal to or below said high velocity locus such that blood flow in said vascular system can be accurately and reliably measured, and said calculating step includes calculating said velocity from one of a two dimensional echocardiographic image and the width of color on an inflow map.

10. The method of claim 9 wherein said calculating step includes calculating pulmonary venous inflow of mitral regurgitation.

* * * * *

UNITED STATES PATENT AND TRADEMARK OFFICE
CERTIFICATE OF CORRECTION

PATENT NO. : 5,373,847
DATED : December 20, 1994
INVENTOR(S) : Edward G. Cape

It is certified that error appears in the above-identified patent and that said Letters Patent is hereby corrected as shown below:

Column 2, line 57, a period --.-- should be inserted after "setting".

Column 4, line 29, --to-- should be inserted before "occur".

Column 5, line 43, a period --.-- should be inserted after "rate".

Claim 3, column 7, line 25, "above" should be --about--.

Signed and Sealed this

Eighth Day of October, 1996

Attest:

BRUCE LEHMAN

Attesting Officer

Commissioner of Patents and Trademarks